US010996816B2

United States Patent
Nathani (10) Patent No.: US 10,996,816 B2
(45) Date of Patent: May 4, 2021

(54) APPARATUS FOR ANALYZING MOOD

(71) Applicant: CYBAGE SOFTWARE PRIVATE LIMITED, Pune (IN)

(72) Inventor: Arun Vijay Nathani, Maharashtra (IN)

(73) Assignee: CYBAGE SOFTWARE PRIVATE LIMITED

( * ) Notice: Subject to any disclaimer, the term of this patent is extended or adjusted under 35 U.S.C. 154(b) by 0 days.

(21) Appl. No.: 16/630,327

(22) PCT Filed: Jul. 13, 2018

(86) PCT No.: PCT/IB2018/055185
§ 371 (c)(1),
(2) Date: Jan. 10, 2020

(87) PCT Pub. No.: WO2019/012489
PCT Pub. Date: Jan. 17, 2019

(65) Prior Publication Data
US 2021/0004140 A1    Jan. 7, 2021

(30) Foreign Application Priority Data

Jul. 14, 2017   (IN) .............................. 201721025118

(51) Int. Cl.
*G06F 3/048* (2013.01)
*G06F 3/0481* (2013.01)
(Continued)

(52) U.S. Cl.
CPC ........ *G06F 3/04817* (2013.01); *G06F 3/0482* (2013.01); *G06F 3/147* (2013.01); *G06F 21/32* (2013.01); *G06Q 10/06398* (2013.01)

(58) Field of Classification Search
CPC .... G06F 3/04817; G06F 3/0482; G06F 21/32; G06F 3/147; G06Q 10/0639
See application file for complete search history.

(56) References Cited

U.S. PATENT DOCUMENTS

2009/0002178 A1    1/2009  Guday

FOREIGN PATENT DOCUMENTS

| EP | 2993602 A1 | 3/2016 |
|---|---|---|
| WO | 2015067534 A1 | 5/2015 |

OTHER PUBLICATIONS

International Search Report and Written Opinion of the International Searching Authority, dated Oct. 23, 2018, International patent application No. PCT/IB2018/05518, 7 pages.

*Primary Examiner* — Pei Yong Weng
(74) *Attorney, Agent, or Firm* — Blueshift IP, LLC; Robert Plotkin (57) ABSTRACT

The present disclosure relates to analyzing mood of a group of users. An apparatus (100) comprises a storage location (102) for storing emoticons, user devices (104), a transceiver (106), a tagging module (108), a collator (110), and a report generator (112). The transceiver (106) receives boot signal generated by the user devices (104) to extract the stored emoticons to construct and transmit a data frame having emoticons, a lock command, and an unlock command. The tagging module is (108) configured to tag the selected emoticon with a user identifier. The collator (110) is configured to collate a plurality of tagged emoticons for each of the users over a predetermined time period and generate an emotional index for each of the users. The report generator (112) is configured to generate a report based on the emotional index for each of the users.

9 Claims, 11 Drawing Sheets

(51) Int. Cl.
*G06F 3/0482* (2013.01)
*G06F 21/32* (2013.01)
*G06F 3/147* (2006.01)
*G06Q 10/06* (2012.01)

APPARATUS FOR ANALYZING MOOD

FIELD

The present disclosure relates to the field of an apparatus for analyzing mood.

DEFINITIONS

As used in the present disclosure, the following terms are generally intended to have the meaning as set forth below, except to the extent that the context in which they are used indicate otherwise.

The expression 'user' used hereinafter in the specification refers to a member of a group, a participant, or attendees of an event.

The expression 'user device' used hereinafter in the specification refers to a device, used by a user, wherein the user device includes but is not limited to a mobile phone, a laptop, a tablet, a PDA, a notebook, a net book, a smart device, a smart phone, a personal computer, and the like.

The expression 'group' used hereinafter in the specification refers to an entity comprising multiple users working towards a collective goal.

The expression 'emotional index' used hereinafter in the specification refers to an indicator that measures the emotional state of the users of a group.

The expression 'event' used hereinafter in the specification refers to, but is not limited to, a multi-purpose program/show made up of a variety of acts.

These definitions are in addition to those expressed in the art.

BACKGROUND

The background information herein below relates to the present disclosure but is not necessarily prior art.

Emotions determine most human behavior. In a group, the decisions/actions of the co-members/leaders may lead to many different emotional responses amongst the other members of the group. These emotional responses play a major role in impacting activities of an event. For example, during an event, a group of people is involved. The audience may be confused, bored, entertained, happy, excited, angry or the like. To determine, whether the event is well organized and to identify the possibilities of improvement in the event, grading systems have been developed. The audience can give rating to the event by using the grading systems.

However, the results of the grading systems are often unreliable. The grading can be low, as the user may not provide accurate grading.

Typically, in an organization, a manager/concerned person cannot identify current mood of his/her team/employees, which in turn restricts him/her from taking appropriate actions to alleviate the mood of the team, thereby losing an opportunity to motivate the team and increase overall productivity.

Therefore, there is a need to develop an apparatus for analyzing mood, which alleviates the above mentioned drawbacks.

OBJECTS

Some of the objects of the present disclosure aimed to ameliorate one or more problems of the prior art or to at least provide a useful alternative are listed herein below.

An object of the present disclosure is to provide an apparatus for analyzing mood of an individual and a group to which individual belong.

Another object of the present disclosure is to provide an apparatus for analyzing mood, which allows users to set their mood.

Yet another object of the present disclosure is to provide an apparatus for analyzing mood, which allows a manager/concerned person to view the overall emotional index of a group.

Other objects and advantages of the present disclosure will be more apparent from the following description when read in conjunction with the accompanying figures, which are not intended to limit the scope of the present disclosure.

SUMMARY

The present disclosure envisages an apparatus for analyzing mood. The apparatus includes a storage location, a plurality of user devices, a transceiver, a tagging module, a collator, and a report generator. The storage location is configured to store sets of emoticons. Each of the user devices includes a display, a selection device, and a booting module. The booting module is configured to generate a boot signal upon completion of a power on self-test. The transceiver is linked to each of the user devices. The transceiver includes a receiver, an extractor, a frame constructor, and a transmitter. The receiver is configured to receive the boot signal from a booting module of a user device. The extractor is configured to extract a set of emoticons from the storage location upon receiving the boot signal. The frame constructor is configured to construct a data frame which includes the extracted set of emoticons, a lock command and an unlock command. The transmitter is configured to transmit the data frame to the booting user device. The booting module of the user device is configured to receive the data frame. The booting module includes an updater, a locking unit, and an unlocking unit. The updater is configured to extract the set of emoticons from the data frame and is further configured to display the extracted set of emoticons on the display of the user device and generates a trigger signal. The locking unit is configured to lock at least one functionality of the user device for a predetermined amount of time period after receiving the trigger signal. The unlocking unit is configured to scan actions performed by the user using the selection device with respect to currently displayed emoticons, and is further configured to unlock the locked functionality of the user device upon selection of an emoticon by the user. The tagging module is configured to cooperate with the booting module. The tagging module is configured to tag the selected emoticon with a user identifier. The collator is configured to cooperate with the tagging module. The collator is configured to collate a plurality of tagged emoticons for each of the users over a predetermined time period and generate an emotional index for each of the users. The collator is further configured to collate tagged emoticons of the group of users and generate a group emotional index. The report generator is configured to cooperate with the collator, and is further configured to generate a report based on the emotional index for each of the users and the group emotional index in predetermined time periods. The extractor, the frame constructor, the updater, the locking unit, the unlocking unit, the tagging module, the collator and the report generator are configured to be implemented on one or more processor(s).

In an embodiment, the apparatus includes a registration module configured to register each of the users by receiving user's details and mood data associated with each of the users from their respective user devices. The registration module includes an input module, an identification module, and an authentication module. The input module is configured to receive the user's details and mood data associated with each of the users from each of the user devices. The identification module is configured to cooperate with the input module, and is further configured to generate a user identifier corresponding to each of the users associated with the user devices. The authentication module is configured to cooperate with the identification module, and is further configured to authenticate each of the users.

In an embodiment, the input module is configured to receive the mood data of each of the users for pre-defined number of times within the pre-defined period of time from each of the user devices.

In an embodiment, the registration module includes a prompt generator configured to generate a prompt on the user devices at a pre-defined time, to update the mood data.

In an embodiment, the apparatus comprises an alert generator configured to cooperate with the report generator to receive the generated report, and is further configured to identify the grim mood of the plurality of users to generate an alert to an administrator/concerned person.

In an embodiment, the set of emoticon includes a very happy mood emoticon, a happy mood emoticon, a neutral mood emoticon, a sad mood emoticon, an angry mood emoticon, and no mood emoticon.

In an embodiment, the storage location is configured to store a look up table having the tagged emoticons for each of the users, and tagged emoticons of the group of users.

In an embodiment, the apparatus includes an editor configured to edit the set of emoticons upon receiving an edit command from the user device.

In an embodiment, the present disclosure also envisages a method for analyzing mood of a group of users.

BRIEF DESCRIPTION OF THE ACCOMPANYING DRAWING

An apparatus for analyzing mood will now be described with the help of the accompanying drawing, in which.

LIST OF REFERENCE NUMERALS

| Reference Numeral | Reference |
|---|---|
| 100 | Apparatus |
| 102 | Storage location |
| 104 | A plurality of user devices |
| 104a | Display |
| 104b | Selection device |
| 104c | Booting module |
| 104c1 | Updater |
| 104c2 | Locking unit |
| 104c3 | Unlocking unit |
| 106 | Transceiver |
| 106a | Receiver |
| 106b | Extractor |
| 106c | Frame constructor |
| 106d | Transmitter |
| 108 | Tagging module |
| 110 | Collator |
| 112 | Report generator |
| 114 | Registration module |
| 114a | Input module |
| 114b | Identification module |
| 114c | Authentication module |
| 114d | Prompt generator |
| 116 | Alert generator |
| 118 | Editor |

DETAILED DESCRIPTION

The present disclosure discloses an apparatus for analyzing mood of a plurality of users. The apparatus as disclosed in the present disclosure is an impersonal apparatus. The apparatus as disclosed in the present is a low power and high speed apparatus. The apparatus, as disclosed in the present disclosure, employs a transceiver in the form of an application specific integrated circuit which fires an extracted emoticon set on a group of randomly and remotely located user devices upon power on self-test operation by the user devices. Further, the apparatus as disclosed in the present disclosure is a high speed apparatus as the transceiver communicates with the group of user devices and does not require the intervention of any human resource to obtain the mood information.

Figure 1:
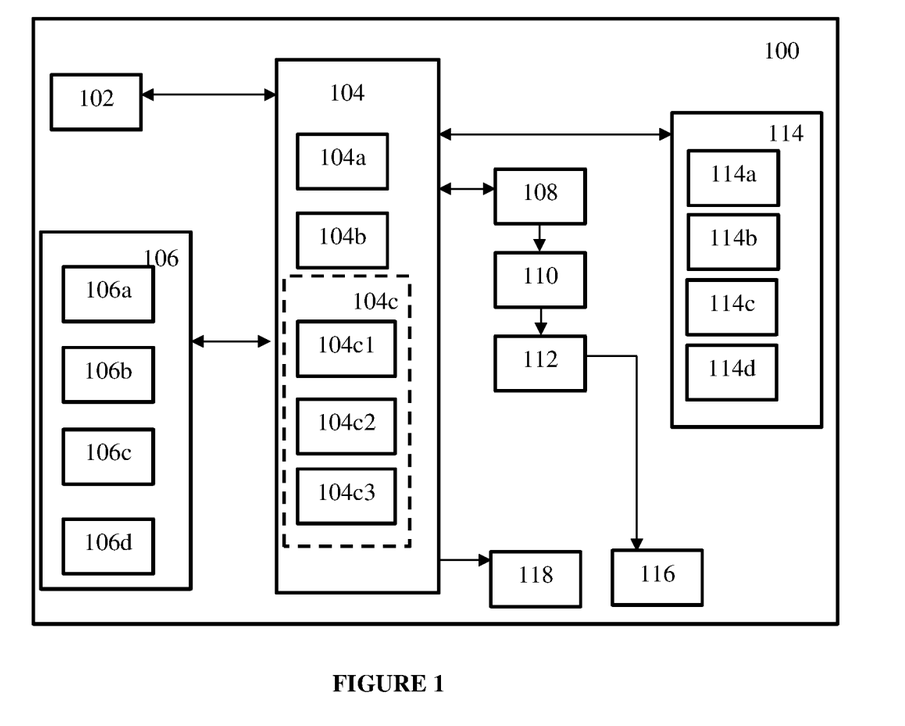
FIG. 1 illustrates a block diagram of an apparatus for analyzing mood.

An apparatus for analyzing mood of a plurality of users is now described with the help of accompanying drawing in which FIG. 1 illustrates a schematic block diagram of the apparatus (100) for analyzing mood of a group of users (hereinafter referred as "apparatus").

The apparatus (100) comprises a storage location (102), a plurality of user devices (104), a transceiver (106), a tagging module (108), a collator (110), and a report generator (112).

The storage location (102) is configured to store sets of emoticons.

The plurality of user devices (104) is selected from the group consisting of a mobile phone, a laptop, a tablet, a PDA, a notebook, a net book, a smart device, a smart phone, a personal computer, and the like.

Figure 2:
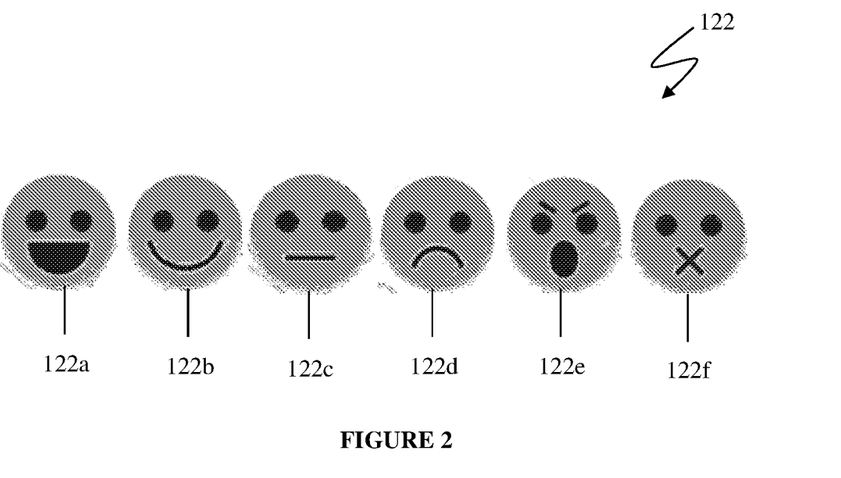
FIG. 2 illustrates various mood emoticons, according to an embodiment of the present disclosure.

In an embodiment, the apparatus (100) includes a registration module (114). The registration module (114) is configured to register each of the users by receiving user's details and mood data associated with each of the users from their respective user devices (104). In an embodiment, the registration module (114) includes an input module (114a), an identification module (114b), an authentication module (114c), and a prompt generator (114d). The input module (114a) is configured to receive user details and user mood data from each of the users. In an embodiment, the user mood data represents whether the user is very happy, happy, angry, sad, or has no mood. In an embodiment, the user can select his/her mood from a drop down list, wherein the moods are displayed on a display (104a) in the form of mood emoticons (122) illustrated in FIG. 2. A very happy mood emoticon is represented by (122a), a happy mood emoticon is represented by (122b), a neutral mood emoticon is represented by (122c), a sad mood emoticon is represented by (122d), an angry mood emoticon is represented by (122e), and no mood emoticon is represented by (122f). In yet another embodiment, the user can set his/her mood for a predefined number of times within a predefined time period, to ensure better engagement and emotional stability. In an embodiment, the user details include user ID, user name, and the like. In an embodiment, the apparatus (100) includes an editor (118). The editor (118) is configured to edit the set of emoticons upon receiving an edit command from the user device (104).

In an embodiment, each of the users can register his/her user devices (104) as registered user devices, for setting mood and receiving prompts for setting mood. Each of the users has to set the mood data at a predefined time, when he/she logins into the apparatus (100).

The registered user devices can be password protected, so that only an authorized person can access the registered user devices for setting mood. The prompt generator (114d) is configured to generate a prompt on the registered user devices, to remind the user to set his/her mood. The reminder can be generated at a predefined time, which can be set by the user, a concerned person, or an administrator. After generating the initial prompt, the prompt generator (114d) keeps on generating reminder periodically, till the user sets his/her mood. The user can set his/her mood from any of the registered user devices.

The identification module (114b) is configured to cooperate with the input module (114a) to receive the user details and mood data from each of the users, and is further configured to generate a user identifier corresponding to each of the users associated with the user devices (104). The authentication module (114c) is configured to cooperate with the identification module (114b) to receive the identification number of each of the users, and is further configured to identify each of the users. In an embodiment, each of the users is required to authenticate themselves before selecting the mood to ensure unauthorized persons cannot do mischief by selecting moods for a user. The authentication can be done by using login-id and password.

Each of the user devices (104) includes the display (104a), a selection device (104b), and a booting module (104c).

The display (104a) is configured to display a set of emoticons and a query to each of the users related to the event. The query is pre-set by an administrator. In an embodiment, the event is selected from the group consisting of multi-purpose programs/shows. In one embodiment, the multi-purpose programs/shows are made up of a variety of acts.

The booting module (104c) is configured to generate a boot signal upon completion of power on self-test.

The transceiver (106) is linked to each of the user devices. The transceiver (106) includes a receiver (106a), an extractor (106b), a frame constructor (106c), and a transmitter (106d).

The receiver (106a) is configured to receive the boot signal from a booting module (104c) of the user device (104). The extractor (106b) is configured to extract a set of emoticons from the storage location (102) upon receiving the boot signal. The frame constructor (106c) is configured to construct a data frame which includes the extracted set of emoticons, a lock command, and an unlock command. The transmitter (106d) is configured to transmit the data frame to the booting user device (104).

The booting module (104c) of the user device is configured to receive the data frame. The booting module (104c) includes an updater (104c1), a locking unit (104c2), and an unlocking unit (104c3). The updater (104c1) is configured to extract the set of emoticons from the data frame and is further configured to the display the set of emoticons on the display (104a) of the user device (104) and generates a trigger signal. In an embodiment, the locking unit (104c2) is configured to lock a portion of the display where the set of emoticons is displayed on the display (104a) of the user device (104) for a pre-determined amount of time period after receiving the trigger signal. The locking of the portion of the display of the user device does not restrict the user to perform other tasks on the user device (104).

In another embodiment, the locking unit (104c2) is configured to lock at least one functionality of the user device (104) for a pre-determined amount of time period after receiving the trigger signal.

In an embodiment, locking of at least one functionality of the user device (104) includes locking of an application executing on the user device (104) and/or locking of the hardware components of the user device (104).

The unlocking module (104c3) is configured to scan actions performed by the user using the selection device (104b) with respect to currently displayed emoticons, and is further configured to unlock the locked functionality of the user device (104) upon selection of an emoticon by the user.

The tagging module (108) is configured to cooperate with the booting module (104c) of the user device (104). The tagging module (108) is further configured to tag the selected emoticon with the user identifier.

The collator (110) is configured to cooperate with the tagging module (108), and is further configured to collate a plurality of tagged emoticons for each of the users over a pre-determined time period and generate an emotional index for each of the users. The collator (110) is further configured to collate tagged emoticons of the group of users and generate a group emotional index. In an embodiment, the storage location (102) is configured to store a look up table having the tagged emoticons for each of the users. The look up table is further configured to store tagged emoticons of the group of users.

The report generator (112) is configured to cooperate with the collator (110), and is further configured to generate a report based on the emotional index for each of the users and the group emotional index in pre-determined time periods.

In an embodiment, a person/manager/administrator can view individual or collective mood of members, attendees, or a group of individuals, in the form of the emotional index. In an embodiment, the report shows a graphical representation of the moods of the members/attendees. It can also be used to find out the emotional index of the entire group. This helps the concerned person/group leaders to understand the effect of any changes, announcements, restructuring, and happenings in the group of the users. In an embodiment, the graphical representation can be generated for specific period that can be further analyzed for detecting patterns with respect to the events happening in the group. In an embodiment, the report generator (112) is configured to generate various other types of reports. In one embodiment, the group leader/concerned person cannot see the emotional index of a specific member to protect individual privacy and interference. However, the upper management can see the emotional index of the individual member, and the emotional index of the group. In an embodiment, the graphical representations of the moods of the group can be generated on the basis of age range, department, demographic, social connect and the like.

Figure 3A:
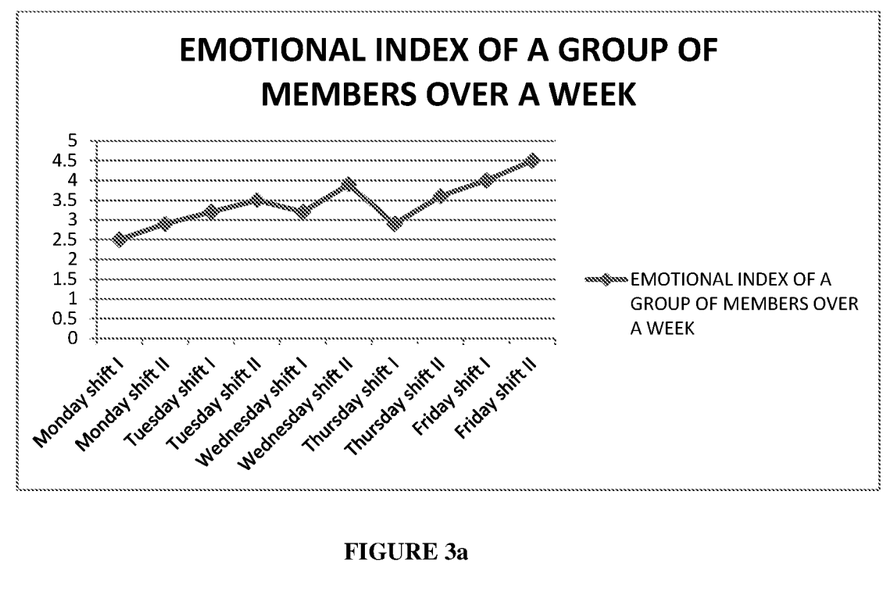
FIG. 3a illustrates a graphical representation indicating emotional index of members in a group over a week, according to an embodiment of the present disclosure.
Figure 3B:
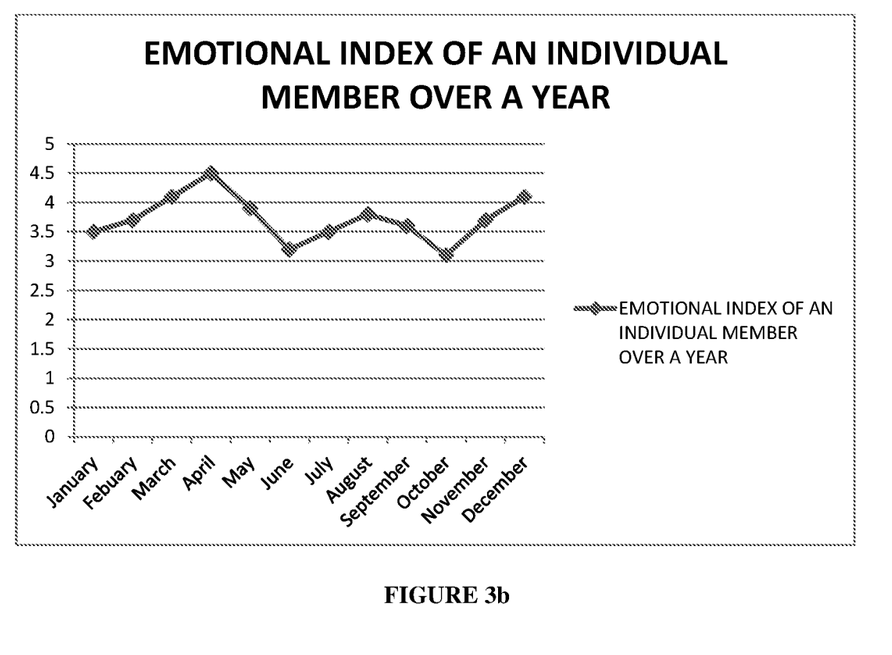
FIG. 3b illustrates a graphical representation indicating emotional index of an individual member over a year, according to an embodiment of the present disclosure.
Figure 3C:
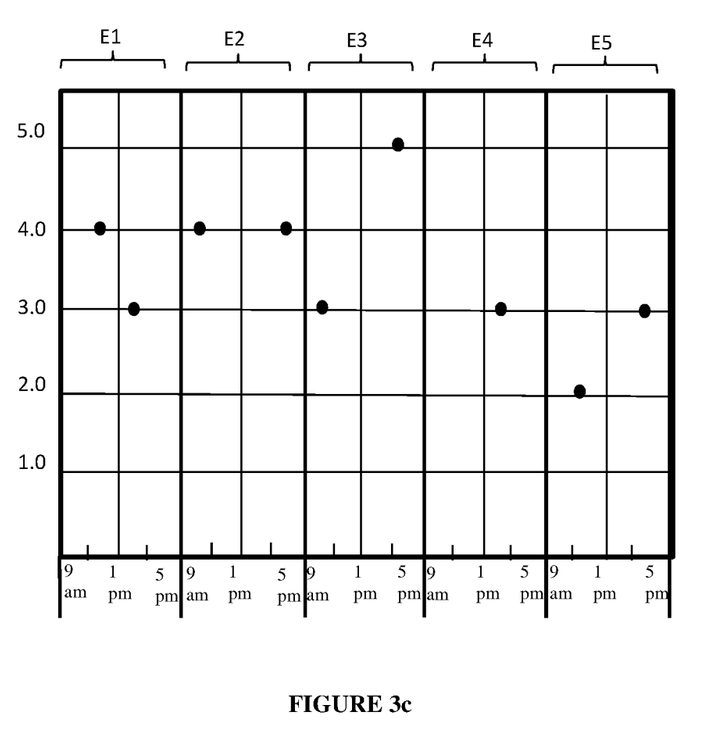
FIG. 3c illustrates a graphical representation indicating emotional index of individual members of a group over a day, according to an embodiment of the present disclosure.
Figure 3D:
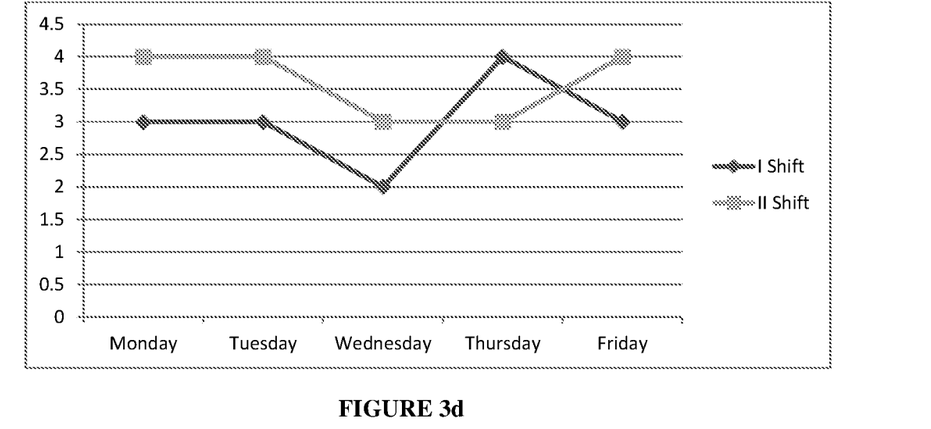
FIG. 3d illustrates a graphical representation indicating emotional index of individual members over a week, according to an embodiment of the present disclosure.
Figure 3E:
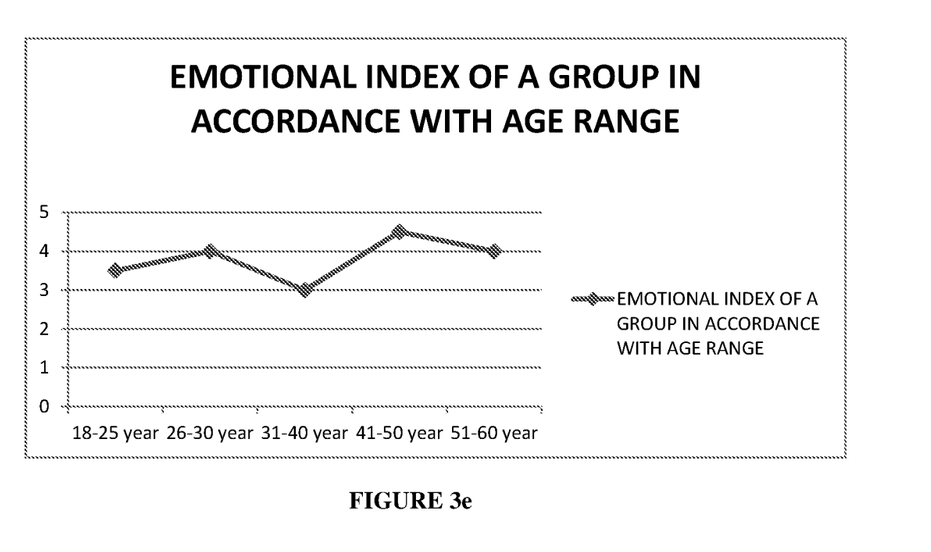
FIG. 3e illustrates a graphical representation indicating emotional index of a group, in accordance with age, according to an embodiment of the present disclosure.

FIG. 3a illustrates an example of a graphical representation indicating the emotional index of members in a group over a week (i.e. group emotional index). FIG. 3b illustrates another example of a graphical representation indicating the emotional index of a member of a group over a year. FIG. 3c illustrates yet another example of a graphical representation indicating the emotional index of a representative members (E1 to E5 (five members)) of a group over a day. It also indicates the time when a member has registered his/her mood. In an embodiment, the graphical representation can be generated for any number of members by the report generator (112). FIG. 3d illustrates a graphical representation indicating the emotional index of an individual member over a week. This helps in identifying productive phases of members in a day, as emotional index which is directly linked to a productivity of the members. It helps the group leader in allocating work to respective members based on their productive phase(s). FIG. 3e illustrates a graphical representation indicating the emotional index of a group in accordance with the age range.

The emotional index is in the range of 1 to 5. The table 1 illustrates different emotional status, in accordance with the emotional index range.

TABLE 1

| Emotional Index Range | Emotional Status |
|---|---|
| 5 to 4 | Very Happy |
| 4 to 3 | Happy |
| 3 to 2 | Neutral |
| 2 to 1 | Sad |

The alert generator (116) is configured to receive the report from the report generator (112) and is further configured to analyze the report to identify the grim mood of a team/group of users on a particular event, and is configured to provide an alert to a concerned person. In an embodiment, the alert generator (116) identifies the persistent grim mood of a user or a team and generates an alert. Based on the generated alert, the concerned person can take necessary action to pacify the team or the user to ensure that the overall productivity is not affected.

In an exemplary embodiment, during an event, a group of people is involved. The audience may be confused, bored, entertained, happy, excited, angry or the like. To determine, whether the event is well organized and to identify the possibilities of improvement in the event, the apparatus (100) is configured to analyze mood of the audience. The audience, by using the apparatus (100), selects an emoticon. This helps the management/concerned person to understand the effect of each activity performed in the event. The management/concerned person can view individual or collective mood of audience, in the form of the emotional index. In one embodiment, the apparatus (100) is further configured to analyze the emoticons selected by each attendee for detecting patterns with respect to the event.

FIG. 3a illustrates an example of a graphical representation indicating the emotional index of members in a group over a week. FIG. 3b illustrates another example of a graphical representation indicating the emotional index of a member of a group over a year. FIG. 3c illustrates yet another example of a graphical representation indicating the emotional index of a representative members (E1 to E5 (five members)) of a group over a day. It also indicates the time when a member has registered his/her mood. In an embodiment, the graphical representation can be generated for any number of members by the report generator (112). FIG. 3d illustrates a graphical representation indicating the emotional index of an individual member over a week. This helps in identifying productive phases of members in a day, as emotional index is directly linked to a productivity of the members. It helps the group leader in allocating work to respective members based on their productive phase(s). FIG. 3e illustrates a graphical representation indicating the emotional index of a group in accordance with the age range.

Figure 4A:
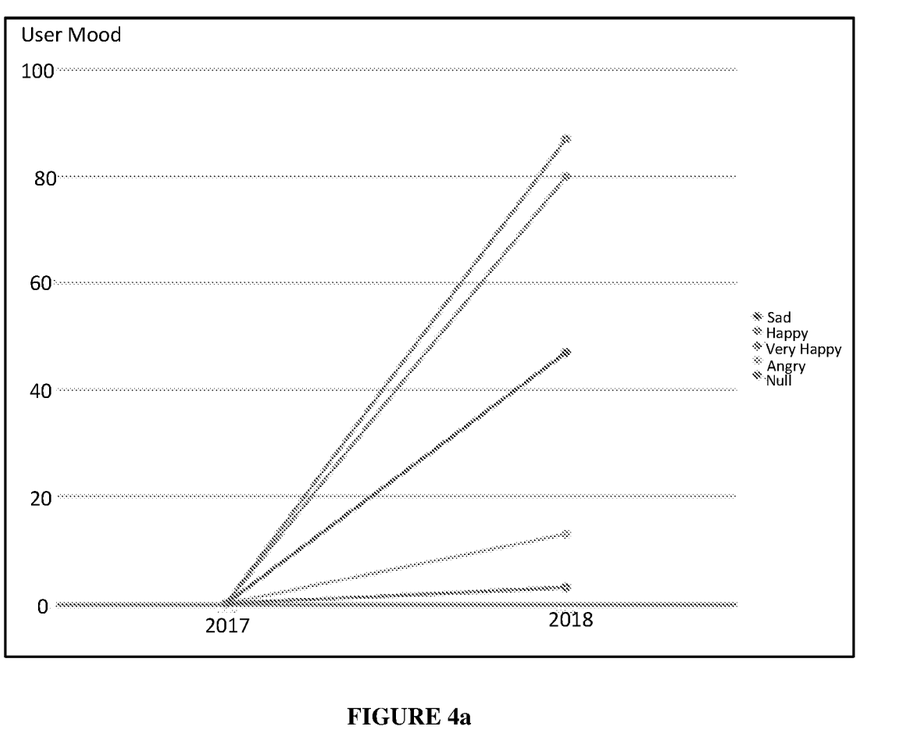
FIGS. 4a-4c illustrate a graphical representation of analysis reports, according to an embodiment of the present disclosure.
Figure 4B:
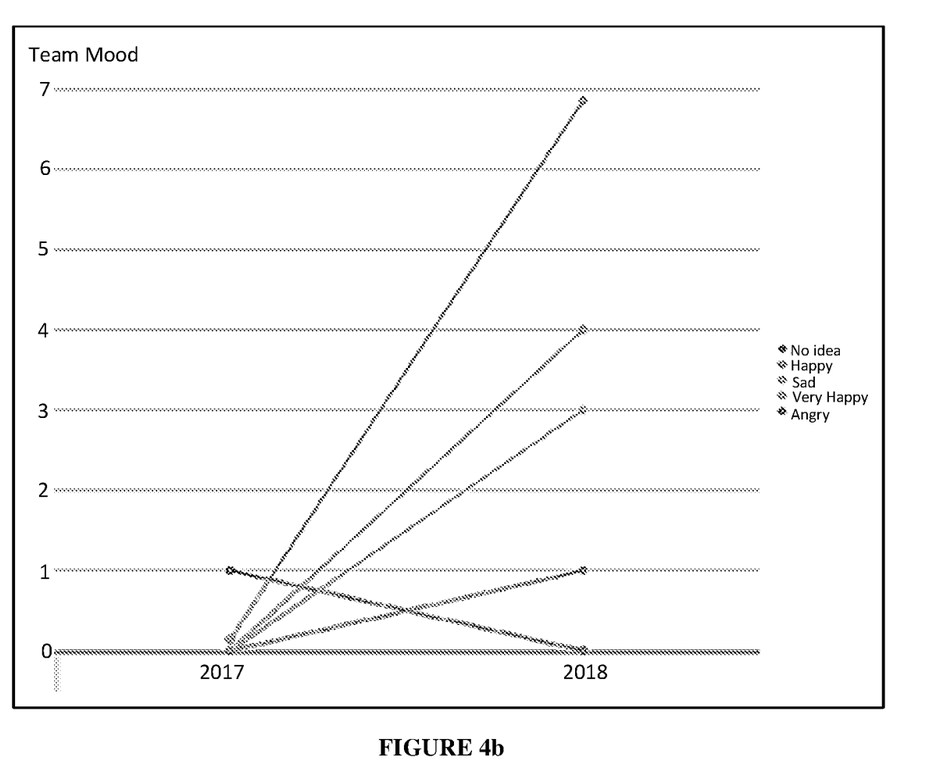
Figure 4C:
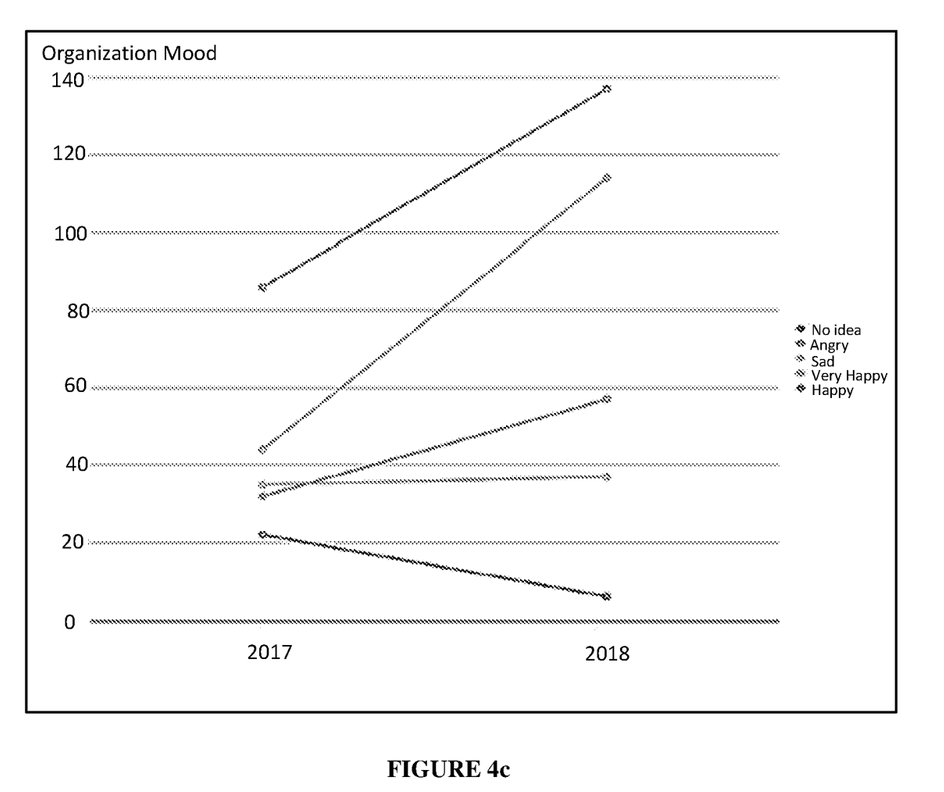

In an exemplary embodiment, FIG. 4a illustrates a graphical representation indicating a report for users. The users can view their mood trends for a pre-defined period of time, such as week, month, quarter, or year. FIG. 4b illustrates a graphical representation indicating a report for managers. The managers can view the collective report of their respective team or attendees of the event. In an embodiment, the managers cannot view the individual mood of any user. It ensures the anonymity so that the user does not hesitate to express his/her emotions and yet gives a manager an idea of the team's sentiments or attendees sentiments. FIG. 4c illustrates a graphical representation indicating a report for an administrator. In an embodiment, the administrator has access to the consolidated mood report of all the users in the organization. This helps the administrator and decision makers to understand the user sentiments. In one embodiment, the administrator has access to a specific user's mood report.

In an embodiment, the report generated by the report generator (112) is utilized to understand the pulse of an event, activities, project, department or the organization, and also provides multiple valuable insights to the administrator. It helps in identifying underlying issues before the administrator turn into potentially big problems. The administrator intervenes or plans strategic initiatives based on findings or trends from the apparatus (100).

In one embodiment, the apparatus (100) is configured to analyze user's sentiments to identify trends. For example, sentiments are always low during the last week of the month or sentiments are consistently low on Monday. The administrator can then identify the root cause for low sentiments and plan certain initiatives to engage employees positively.

In another embodiment, the apparatus (100) is configured to analyze manager's bonding with the team. Ideally the manager's sentiment would be in correlation with the team's sentiment. If the manager's sentiment is way different than the team, then the chances are that the manager is out-of-sync with his team. It is a potential risk as the team eventually might get disengaged and will not even feel motivated. The administrator can easily identify such anomalies and take corrective actions as applicable.

In yet another embodiment, the apparatus (100) is configured to analyze impact of events or changes in the organization. Positive sentiments after a change or an initiative depict that such changes matter to the employees. Changes or events not taken positively can derail employees' performance and productivity. The organization more often than not put some measures to analyze impact of changes.

In an embodiment, the extractor (106b), the frame constructor (106c), the updater (104c1), the locking unit (104c2), the unlocking unit (104c3), the tagging module (108), the collator (110), and the report generator (112), are configured to be implemented on one or more processor(s).

The processor is configured to generate processing commands The processor may be implemented as one or more microprocessors, microcomputers, microcontrollers, digital signal processors, central processing units, state machines, logic circuitries, and/or any devices that manipulate signals based on operational instructions.

Figure 5A:
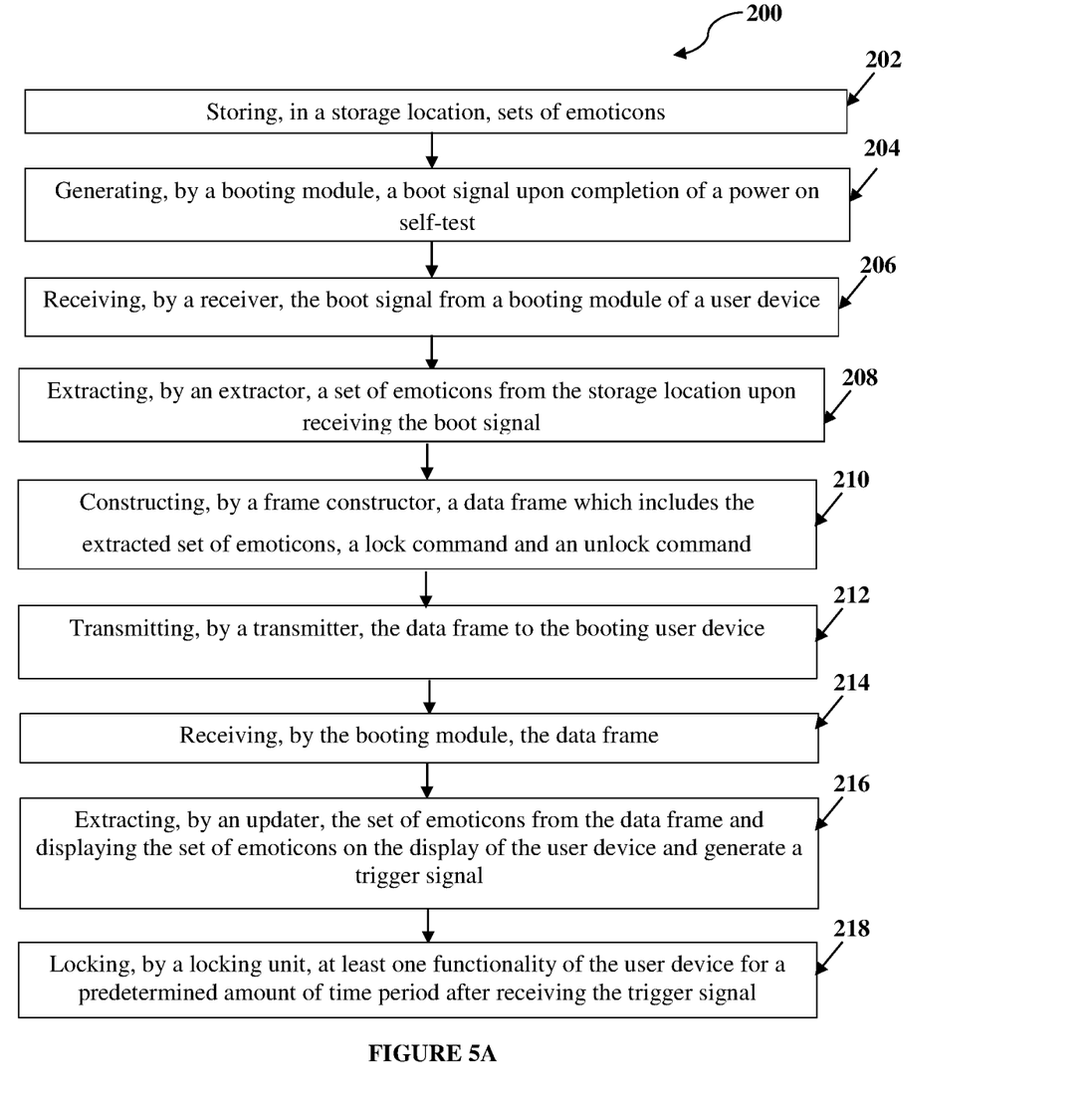
FIGS. 5a-5b illustrate a flow diagram showing steps performed by the apparatus for analyzing mood of FIG. 1.
Figure 5B:
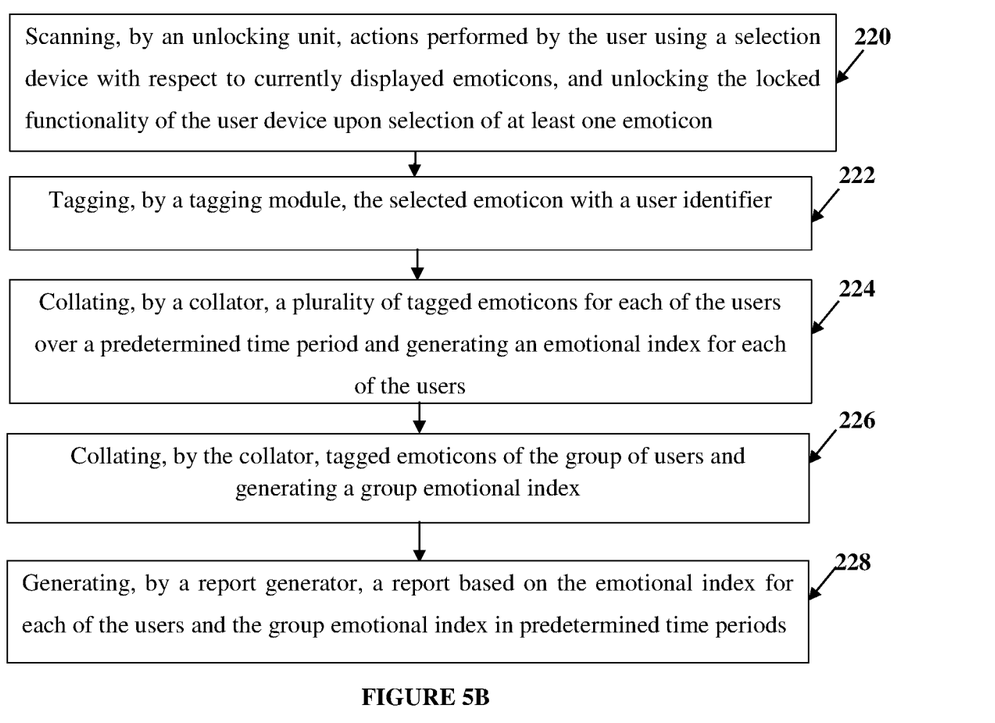

FIG. 5 illustrates a flow diagram (200) showing steps performed by the apparatus for analyzing mood (100). The method steps are as follows:

At block 202, storing, in a storage location (102), sets of emoticons.

At block 204, generating, by a booting module (104c), a boot signal upon completion of a power on self-test.

At block 206, receiving by a receiver (106a), the boot signal from a booting module (104c) of a user device (104).

At block 208, extracting by an extractor (106b), a set of emoticons from the storage location (102) upon receiving the boot signal.

At block 210, constructing, by a frame constructor (106c), a data frame which includes the extracted set of emoticons, a lock command and an unlock command At block 212, transmitting, by a transmitter (106d), the data frame to the booting user device.

At block 214, receiving, by the booting module (104c), the data frame.

At block 216, extracting, by an updater (104c1), the set of emoticons from the data frame and displaying said extracted set of emoticons on said display (104a) of the user device (104) and generate a trigger signal.

At block 218, locking by a locking unit (104c2), at least one functionality of the user device for a predetermined amount of time period after receiving the trigger signal.

At block 220, scanning, by an unlocking unit (104c3), actions performed by the user using a selection device (104b) with respect to currently displayed emoticons, and unlocking the locked functionality of the user device (104) upon selection of an emoticon by the user.

At block 222, tagging, by a tagging module (108), the selected emoticon with a user identifier.

At block 224, collating, by a collator (110), a plurality of tagged emoticons for each of the users over a predetermined time period and generating an emotional index for each of the users.

At block 226, collating, by the collator (110), tagged emoticons of the group of users and generating a group emotional index.

At block 228, generating, by a report generator (112), a report based on the emotional index for each of the users and the group emotional index in predetermined time periods.

TECHNICAL ADVANCEMENTS

The present disclosure provides a technical solution to a technical problem. There are no conventional systems for analyzing the mood of an employee or a person and such information about the mood of the employee can only be done on person-to-person basis. In the personal system, an authority or a team leader analyzes the mood of an employee or a person by asking questions to the employee. In such events, a person such as an employee may not answer the questions properly as the person's response may be subjective and the mood of the person is not determined accurately. The aforementioned conventional systems are completely manual. Even if such information is gathered manually and is also graded manually the manual system is time consuming and requires a lot of human resources for identifying mood of the employee. In a grading based system, a user provides the grading for a service such as at an airport and the grading provided by the user is accessed by an administrator. However, such systems are also not accurate as they do not ensure that every user will grade a service and it is not possible to generate an emotional index with respect to a specific time period. Further, in a conventional digital grading system, the power utilization is very high. For example in digital grading system, a digital kiosk with a touch screen capabilities is required at an event place. Such a digital kiosk is coupled to a network and consumes high power. Further, an administrator machine is coupled to the network. So, the total power consumed is equal to the power consumed by the digital kiosk plus power consumed by the network elements plus the power consumed by the administrator machine.

The present disclosure provides a technical solution to a technical problem. The apparatus as disclosed in the present disclosure is an impersonal system. The apparatus as disclosed in the present is a low power and high speed apparatus. The apparatus employs the transceiver in the form of an application specific integrated circuit which fires an extracted emoticon set on a group of randomly and remotely located user devices upon power on self-test operation by the user devices. Thus, the apparatus as disclosed in the present disclosure is a low power system, as it requires only the application specific integrated circuit and user devices. Further, the apparatus as disclosed in the present disclosure is a high speed apparatus as the transceiver communicates with the group of user devices and does not require the intervention of any human resource to obtain the mood information. Further, the locking arrangement ensures that every user in the group will mandatorily provide the information by selecting an emoticon.

The transceiver as disclosed in the apparatus of the present disclosure transmits data frames having emoticons, lock command and unlock command. The lock command locks at least one functionality of the user device for a predetermined time period and upon selection of an emoticon by the user, the unlock command unlocks the locked functionality of the user device thereby providing an interface for capturing the mood of the user upon booting of the user device and ensures that every user in the group compulsorily provides the information.

Further, the apparatus as disclosed in the present disclosure automatically computes the emotional index for a user over a defined period of time or a group of users which is not possible in the conventional manual systems.

The technology as disclosed in the present disclosure modifies the user device. For instance, the booting module resident in the user device is modified. The booting module upon completion of the power on self-test is modified to display the extracted set of emoticons on the display of the user device until the user selects a particular mood emoticon. The booting module is further modified to lock at least one functionality of the user device for a predetermined amount of time period until the selection occurs. Once the emoticon is selected by the user, the booting module is modified to unlock the locked functionality of the user device and remove the emoticon set from the display of the user device. Only the selected emoticon tagged with the user ID is transmitted to the collator.

The disclosure has been described with reference to the accompanying embodiments which do not limit the scope and ambit of the disclosure. The description provided is purely by way of example and illustration.

The embodiments herein above and the various features and advantageous details thereof are explained with reference to the non-limiting embodiments in the following description.

Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The foregoing description of the specific embodiments so fully revealed the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the disclosure to achieve one or more of the desired objects or results.

Any discussion of documents, acts, materials, devices, articles or the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification, specific to the contrary.

While considerable emphasis has been placed herein on the components and component parts of the preferred embodiments, it will be appreciated that many embodiments can be made and that many changes can be made in the preferred embodiments without departing from the principles of the disclosure. These and other changes in the preferred embodiment as well as other embodiments of the disclosure will be apparent to those skilled in the art from the disclosure herein, whereby it is to be distinctly understood that the foregoing descriptive matter is to be interpreted merely as illustrative of the disclosure and not as a limitation.

The invention claimed is:

1. An apparatus (100) for analyzing mood of a group of users, said apparatus (100) comprising:
   a storage location (102) configured to store sets of emoticons;
   a plurality of user devices (104), wherein each of the user devices (104) includes:
      a display (104a);
      a selection device (104b); and
      a booting module (104c) configured to generate a boot signal upon completion of a power on self-test;
   a transceiver (106) linked to each of said user devices (104), said transceiver (106) includes:
      a receiver (106a) configured to receive said boot signal from a booting module (104c) of a user device (104);
      an extractor (106b) configured to extract a set of emoticons from said storage location (102) upon receiving said boot signal;
      a frame constructor (106c) configured to construct a data frame which includes said extracted set of emoticons, a lock command and an unlock command; and
      a transmitter (106d) configured to transmit said data frame to said booting user device;
   said booting module (104c) of said user device (104) configured to receive said data frame, said booting module (104c) includes:
      an updater (104c1) configured to extract said set of emoticons from said data frame and further configured to display said extracted emoticons on said display (104a) of said user device (104) and generate a trigger signal;
      a locking unit (104c2) configured to lock at least one functionality of said user device (104) for a predetermined amount of time period after receiving said trigger signal; and
      an unlocking unit (104c3) configured to scan actions performed by said user using said selection device (104b) with respect to currently displayed emoticons, and further configured to unlock said locked functionality of said user device (104) upon selection of an emoticon by said user;
   a tagging module (108) configured to cooperate with said booting module (104c), said tagging module (108) configured to tag said selected emoticon with a user identifier;
   a collator (110) configured to cooperate with said tagging module (108), said collator (110) configured to collate a plurality of tagged emoticons for each of the users over a predetermined time period and generate an emotional index for each of the users, said collator (110) further configured to collate tagged emoticons of said group of users and generate a group emotional index; and
   a report generator (112) configured to cooperate with said collator (110), and further configured to generate a report based on said emotional index for each of the users and said group emotional index in predetermined time periods;
   wherein said extractor (106b), said frame constructor (106c), said updater (104c1), said locking unit (104c2), said unlocking unit (104c3), said tagging module (108), said collator (110) and said report generator (112) are configured to be implemented on one or more processor(s).

2. The apparatus (100) as claimed in claim 1, wherein said apparatus (100) includes a registration module (114) configured to register each of the users by receiving users details and mood data associated with each of the users from their respective user devices, wherein said registration module (114) comprises:

an input module (114*a*) configured to receive the users details and mood data associated with each of the users from each of the user devices (104);

an identification module (114*b*) configured to cooperate with said input module (114*a*), and is further configured to generate a user identifier corresponding to each of the users associated with said user devices (104); and an authentication module (114*c*) configured to cooperate with said identification module (114*b*), and is further configured to authenticate each of the users.

3. The apparatus (100) as claimed in claim 2, wherein said input module (114*a*) is configured to receive the mood data of each of the users for pre-defined number of times within said pre-defined period of time from each of the user devices.

4. The apparatus (100) as claimed in claim 2, wherein said registration module (114) includes a prompt generator (114*d*) configured to generate a prompt on said user devices (104) at a pre-defined time, to update said mood data.

5. The apparatus (100) as claimed in claim 1, wherein said apparatus (100) comprises an alert generator (116) configured to cooperate with said report generator (112) to receive said generated report, and is further configured to identify the grim mood of said plurality of users to generate an alert to an administrator/concerned person.

6. The apparatus (100) as claimed in claim 1, wherein said set of emoticon includes a very happy mood emoticon (122*a*), a happy mood emoticon (122*b*), a neutral mood emoticon (122*c*), a sad mood emoticon (122*d*), an angry mood emoticon (122*e*), and a no mood emoticon (122*f*).

7. The apparatus (100) as claimed in claim 1, wherein said storage location (102) is configured to store a look up table having said tagged emoticons for each of the users, said look up table is further configured to store tagged emoticons of said group of users.

8. The apparatus (100) as claimed in claim 1, which includes an editor (118) configured to edit said set of emoticons upon receiving an edit command from said user device.

9. A method (200) for analyzing mood of a group of users, said method comprising the steps of:

storing (202), in a storage location (102), sets of emoticons;

generating (204), by a booting module (104*c*), a boot signal upon completion of a power on self-test;

receiving (206), by a receiver (106*a*), said boot signal from a booting module (104*c*) of a user device (104);

extracting (208), by an extractor (106*b*), a set of emoticons from said storage location (102) upon receiving said boot signal;

constructing (210), by a frame constructor (106*c*), a data frame which includes said extracted set of emoticons, a lock command and an unlock command;

transmitting (212), by a transmitter (106*d*), said data frame to said booting user device;

receiving (214), by said booting module (104*c*), said data frame;

extracting (216), by an updater (104*c*1), said set of emoticons from said data frame and displaying said set of emoticons on said display (104*a*) of said user device (104) and generating a trigger signal;

locking (218), by a locking unit (104*c*2), at least one functionality of said user device for a predetermined amount of time period after receiving said trigger signal;

scanning (220), by an unlocking unit (104*c*3), actions performed by said user using a selection device (104*b*) with respect to currently displayed emoticons, and unlocking said locked functionality of said user device (104) upon selection of an emoticon by said user;

tagging (222), by a tagging module (108), said selected emoticon with a user identifier;

collating (224), by a collator (110), a plurality of tagged emoticons for each of the users over a predetermined time period and generating an emotional index for each of the users;

collating (226), by said collator (110), tagged emoticons of said group of users and generating a group emotional index; and generating (228), by a report generator (112), a report based on said emotional index for each of the users and said group emotional index in predetermined time periods.

\* \* \* \* \*